United States Patent [19]
Kenmochi et al.

[11] Patent Number: 5,613,962
[45] Date of Patent: Mar. 25, 1997

[54] DISPOSABLE ABSORBENT ARTICLES

[75] Inventors: Yasuhiko Kenmochi, Kagawa-ken; Hisashi Takai, Ehime-ken; Tomoko Tsuji, Kagawa-ken, all of Japan

[73] Assignee: Uni-Charm Corporation, Ehime-ken, Japan

[21] Appl. No.: 569,037

[22] Filed: Dec. 7, 1995

[30] Foreign Application Priority Data

Dec. 13, 1994 [JP] Japan .................................. 6-309232

[51] Int. Cl.⁶ ...................................................... A61F 13/15
[52] U.S. Cl. ........................................... 604/378; 604/382
[58] Field of Search .................................. 604/378, 380, 604/381–383, 385.1

[56] References Cited

U.S. PATENT DOCUMENTS

| | | | |
|---|---|---|---|
| 4,397,644 | 8/1983 | Matthews et al. | 604/378 |
| 4,585,449 | 4/1986 | Karami | 604/378 |
| 4,622,036 | 11/1986 | Goodrum | 604/378 |
| 4,636,209 | 1/1987 | Lassen | 604/378 |
| 5,281,208 | 1/1994 | Thompson et al. | 604/378 |
| 5,383,870 | 1/1995 | Takai et al. | 604/378 |
| 5,387,209 | 2/1995 | Yamamoto et al. | 604/378 |

FOREIGN PATENT DOCUMENTS 5-154175  6/1993  Japan .

*Primary Examiner*—John G. Weiss
*Assistant Examiner*—Ki Yong O
*Attorney, Agent, or Firm*—Lowe, Price, LeBlanc & Becker

[57] ABSTRACT

A disposable absorbent article 1 comprising a liquid-absorbent core at least an upper surface of which is covered with a topsheet provided with a plurality of liquid guide passages, a body fluid diffusing sheet made of hydrophilic fibers being disposed between a lower surface of the topsheet and the upper surface of the liquid-absorbent core, the sheet being formed on its upper surface with a plurality of parallel extending stripe-zones of a hydrophobic synthetic resin.

4 Claims, 3 Drawing Sheets

DISPOSABLE ABSORBENT ARTICLES

BACKGROUND OF THE INVENTION

The present invention relates to a disposable absorbent articles and, more particularly, to a disposable article such as a sanitary napkin or menstruation pad, a disposable diaper and the like.

It is known in the industry of body fluid absorbent articles to cover an upper surface of a liquid-absorbent core with a topsheet having a plurality of liquid guide passages each extending therethrough in the direction of thickness and being open at its upper and lower ends. In the case of sanitary napkins as an embodiment of such articles, it is well known, for example, from Japanese Laid-Open Patent Application No. Hei5-154175 to cover the openings at the lower ends of the respective liquid guide passages with a netlike sheet so as to divide each opening into a plurality of smaller openings and thereby to prevent the quantity of menstrual discharge having been absorbed in the liquid-absorbent core from being visible to a user through the openings of the liquid guide passages. Certainly, the netlike sheet covers, to some degree, blots of menstrual discharge absorbed by the absorbent core.

However, dividing each opening by the netlike sheet into a plurality of smaller openings may correspondingly reduce the area ratio of the openings over the topsheet and deteriorate the absorption capacity of the napkin such as body fluid absorbing rate or absorptivity.

SUMMARY OF THE INVENTION

In view of the problem as mentioned above, it is a principal object of the invention to cover up blots of menstrual discharge absorbed by the absorbent core without deteriorating the absorption capacity for body fluid by disposing between the upper surface of the liquid-absorbent core and the lower surface of the topsheet a body fluid diffusing sheet made of hydrophilic fibers and provided on its upper side with a plurality of stripe-zones formed by a hydrophobic synthetic resin.

The object set forth above is achieved, according to the invention, by a disposable absorbent article comprising a topsheet provided with a plurality of liquid guide passages spaced one from another by a desired distance in the direction of its plane each extending therethrough in the direction of thickness and having openings at its upper and lower ends, and a liquid-absorbent core at least an upper surface of which is covered with the topsheet, wherein: there disposed a body fluid diffusing sheet of hydrophilic fibers carrying on its upper surface with a plurality of parallel extending stripe-zones made of a hydrophobic synthetic resin between the upper surface of the liquid-absorbent core and a lower surface of the topsheet in contact with the lower ends of the liquid guide passages so that the stripe-zones extending across the openings at a lower ends of the liquid guide passages.

Preferably, the stripe-zones are formed by an extrusion-molded thermoplastic synthetic resin and the body fluid diffusing sheet is made of thermoplastic synthetic fibers previously treated so as to become hydrophilic.

Preferably, the stripe-zones are formed also on a lower surface of the body fluid diffusing sheet.

With the body fluid absorbent article arranged as mentioned above, excreted body fluid, for example, menstrual blood discharged onto the topsheet moves from the openings at the lower ends of the respective liquid guide passages to the body fluid diffusing sheet being in contact with these openings, then diffuses in the body fluid diffusing sheet and finally moves into the underlying liquid-absorbent core. The liquid-absorbent core is covered with the body fluid diffusing sheet which carries on its upper surface the plurality of stripe-zones, so blots of menstrual discharge having been absorbed by the liquid-absorbent core is effectively covered up by cooperation of the diffusing sheet with the stripe-zones carried thereon and thereby made hardly visible. Even if menstrual blood is discharged onto a limited location of the article, such menstrual discharge spreads over a large extent of the liquid-absorbent core and is rapidly absorbed thereinto, since menstrual discharge diffuses in the body fluid diffusing sheet of hydrophilic fibers.

DETAILED DESCRIPTION OF THE PREFERRED EMBODIMENT

A body fluid absorbent article according to the invention will be better understood from the following description of a sanitary napkin as an embodiment of the invention made in reference with the accompanying drawings.

Figure 1:
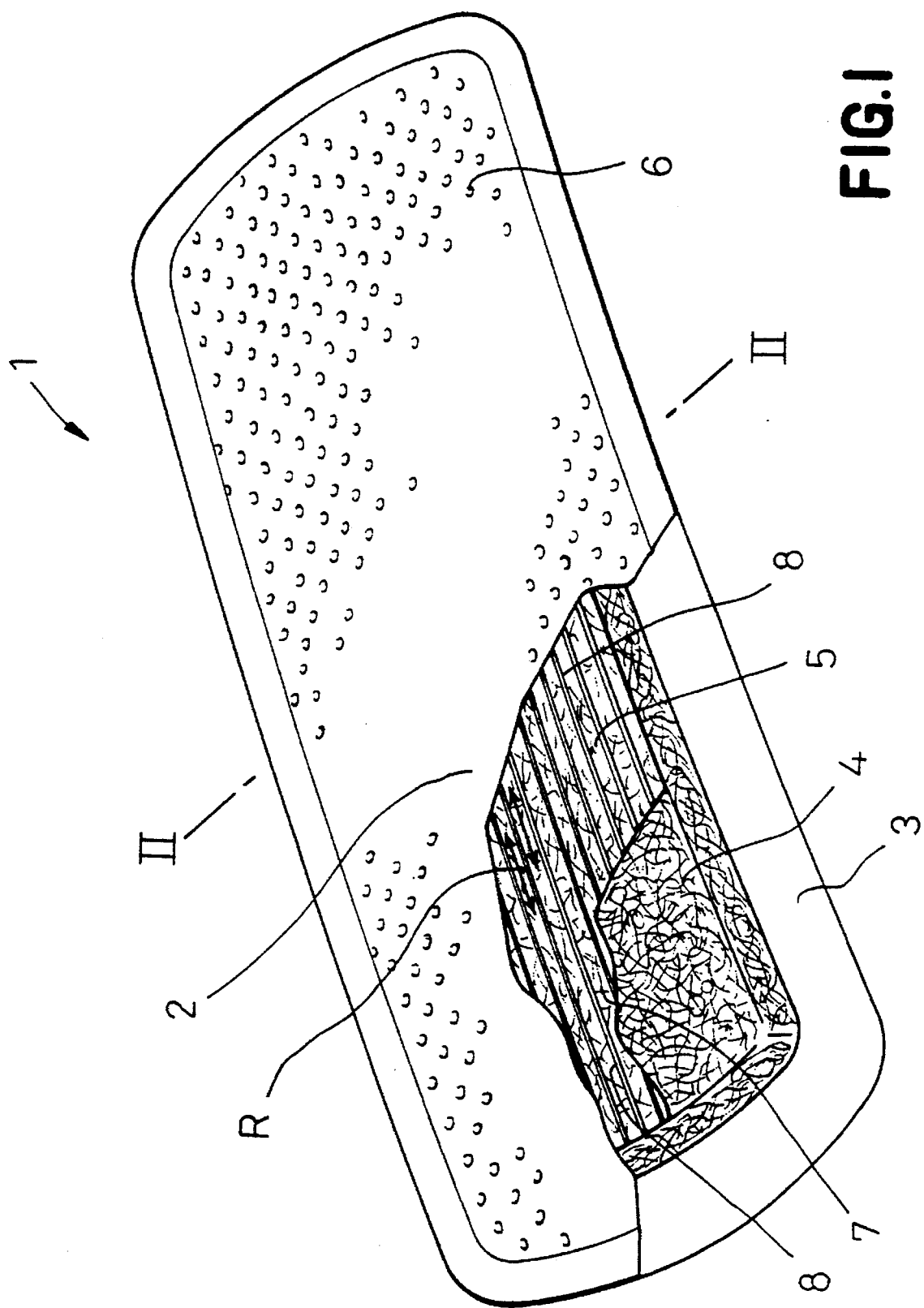
FIG. 1 is a perspective view showing a sanitary napkin according to the invention as partially broken away.

Referring to FIG. 1, a sanitary napkin or menstruation pad 1 is substantially rectangular and comprises a liquid-permeable topsheet 2, a liquid-impermeable backsheet 3, a liquid-absorbent core 4 disposed between these two sheets 2, 3, and a body fluid diffusing sheet 5 disposed between the topsheet 2 and the liquid-absorbent core 4. The liquid-absorbent core 4 and the diffusing sheet 5 have substantially the same shapes in the plan view and an upper surface of the liquid-absorbent core is covered with the diffusing sheet 5. The top- and backsheets 2, 3 are water-tightly bonded together along their portions extending outward beyond a peripheral edge of the liquid-absorbent core 4.

The topsheet 2 is made of a thermoplastic synthetic resin film and provided with a plurality of liquid guide passages 6 spaced one from another by a desired distance in the direction along a plane surface of the topsheet 2 to assure a desired liquid-permeability. The backsheet 3 is made of a thermoplastic synthetic resin film. The liquid-absorbent core 4 is made of fluff pulp fibers or a mixture of fluff pulp fibers and superabsorbent polymer particles. The diffusing sheet 5 is made of thermoplastic synthetic fiber fabrics previously treated so as to become hydrophilic and carries at least on its upper surface a plurality of stripe-zones 8 made of a hydrophobic thermoplastic synthetic resin extending longitudinally of the napkin parallel one to another, each of these stripe-zones 8 being dimensioned to have a width of 0.05 to 1.5 mm, more preferably 0.1 to 1.0 mm.

Figure 2:
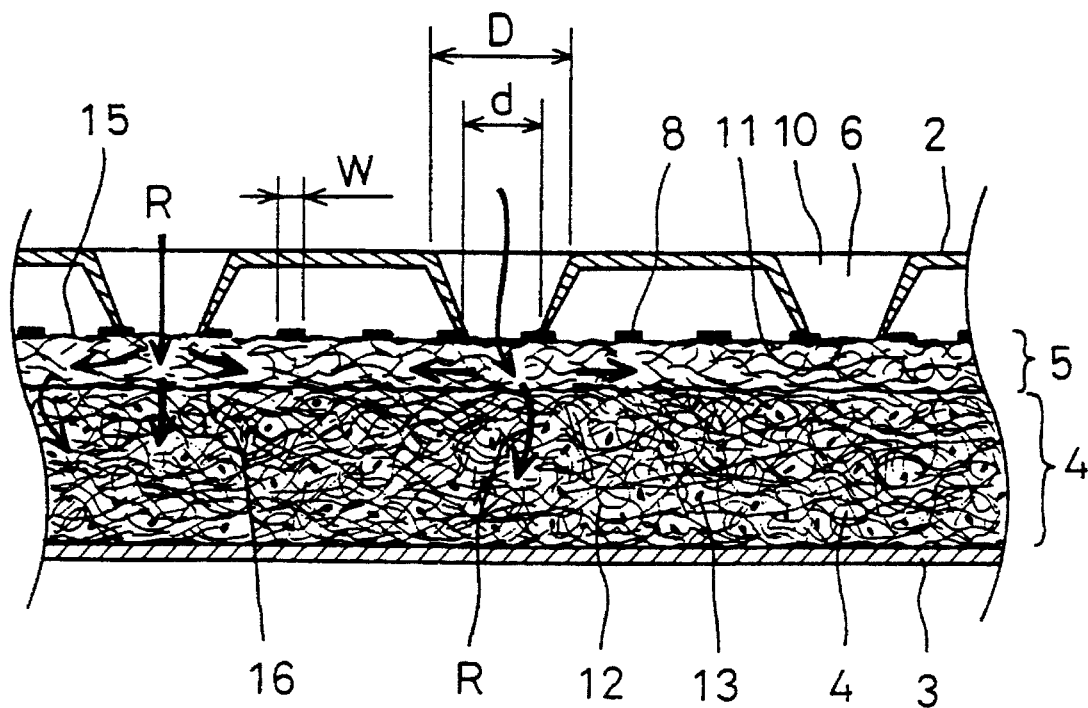
FIG. 2 is a fragmentary sectional view in an enlarged scale taken along a line II—II in FIG. 1.

Referring to FIG. 2, each liquid guide passage 6 of the topsheet 2 has an upper end opening 10 and a lower end opening 11 which may, in turn, have a suitable radial cross-sectional shape such as a circular or polygonal shape. So far as these openings are circular, it is not important whether a diameter "D" of the upper end opening 10 is larger than a diameter "d" of the lower end opening 11 or vice versa.

As shown, individual fluff pulp fibers 12 as well as individual polymer particles 13 of super absorptivity are seen in the cross-section of the liquid-absorbent core 4. A fiber density of the liquid-absorbent core 4 is adjusted to be higher than a fiber density of the diffusing sheet 5 and a quantity of the polymer particles 13 is adjusted to be 5 to 40% by weight of the liquid-absorbent core 4. While a desired effect may be achieved by homogeneously mixing the polymer particles 13 with the fluff pulp fibers 12, it is preferred to mix the polymer particles 13 with the fluff pulp fibers 12 so that the former may be distributed with a density higher in a layer adjacent the bottom than in a layer adjacent the top of the liquid-absorbent core 4. The liquid-absorbent core 4 constructed in such a manner may be then intermittently bonded to the upper surface of the backsheet 3 by suitable means such as hot melt adhesive to ensure that the liquid-absorbent core 4 and the backsheet 3 should not get out of their predetermined relative position.

A nonwoven fabric used for the diffusing sheet 5 may be, for example, a spun bond nonwoven fabric having a weight per unit area of 10 to 50 g/m$^2$ previously treated so as to become hydrophilic and a fiber density adjusted to be lower than a fiber density of the liquid-absorbent core 4. The upper surface 15 of the diffusing sheet 5 is in close contact with the lower end openings 11 of the respective liquid guide passages 6. The stripe-zones 8 on the upper surface 15 are formed by a hydrophobic synthetic resin film such as a polyethylene or polypropyrene welded to the diffusing sheet 5, each having a width "W"=0.05 to 1.5 mm, more preferably, 0.1 to 1.0 mm. These stripe-zones 8 are spaced one from another by a distance smaller than the diameter "d" of each lower end openings 11 so that the stripe-zones 8 may partially extend across portions of the respective lower end openings 11.

With the napkin 1 constructed as described hereinabove, menstrual discharge is guided as indicated by arrows in FIGS. 1 and 2. Specifically, menstrual discharge is absorbed through the liquid guide passages 6 into the diffusing sheet 5 having a relative low density, whereupon menstrual discharge diffuses in the sheet 5 longitudinally (See FIG. 1) as well as transversely (See FIG. 2) of the sheet 5, and finally menstrual discharge is absorbed and held by the liquid-absorbent core 4 having a relatively high density. Menstrual discharge thus held by the liquid-absorbent core 4 is effectively covered up with the diffusing sheet 5 and the stripe-zones 8 so that it can be hardly visible from above through the topsheet 2 and its back flow from the liquid-absorbent core 4 to the upper surface of the topsheet 2 (so-called rewet phenomenon) can be avoided. With the napkin 1, menstrual discharge diffuses over a large extent as soon as it is absorbed in the sheet 5, and is absorbed by the upper surface of the liquid-absorbent core 4 over a correspondingly large extent. In a consequence, both the absorbing rate and the absorption capacity for menstrual discharge of the napkin 1 as a whole are not significantly affected regardless of the fact that the stripe-zones 8 partially cover the lower end openings 11 of the respective liquid guide passages 6.

Figure 3:
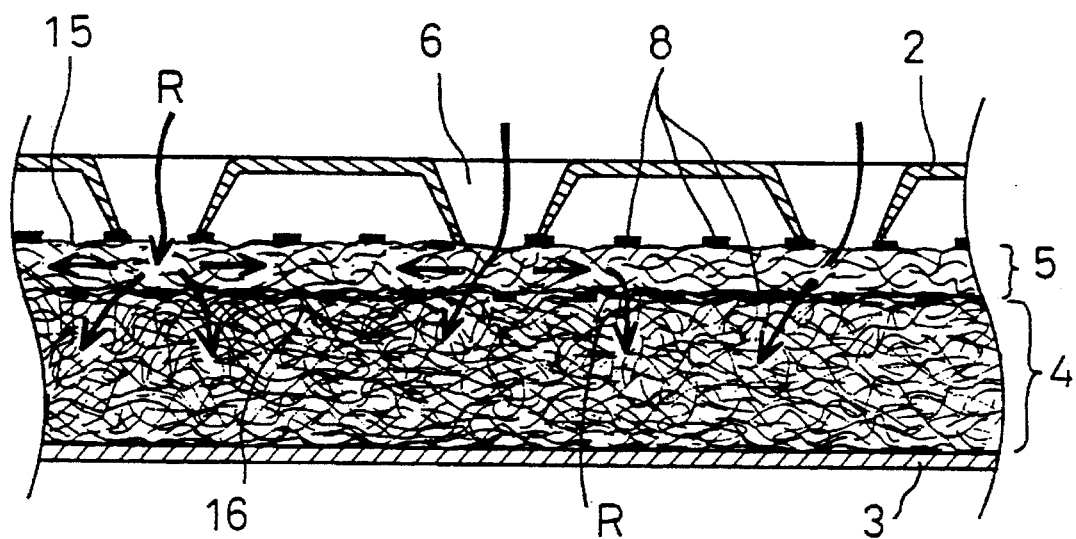
FIG. 3 is a view similar to FIG. 2 but showing an alternative arrangement of the invention.

Referring to FIG. 3, the diffusing sheet 5 is provided not only on its upper surface 15 but also on its lower surface 16 with the stripe-zones 8. With the diffusing sheet 5 in this variant, blots of menstrual discharge absorbed by the liquid-absorbent core 4 can be directly covered up while the absorbing rate for menstrual discharge is improved by decreasing a total area over which the lower end openings 11 of the respective liquid guide passages 6 are directly closed by the stripe-zones 8.

Figure 4:
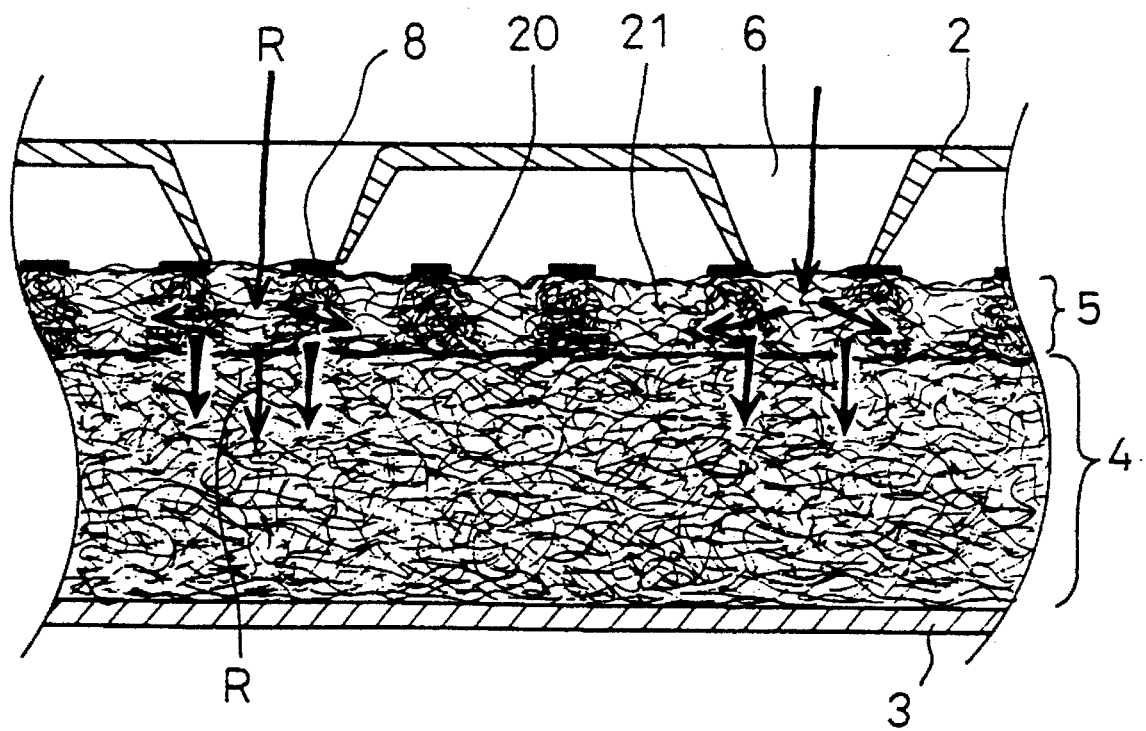
FIG. 4 is a view similar to FIG. 2 but showing another alternative arrangement of the invention.

Referring to FIG. 4, the nonwoven fabric forming the diffusing sheet 5 has a fiber density adjusted to be higher in sections 20 underlying the stripe-zones 8 than in sections 21 extending between these stripe-zones 8. Additionally, the density in the sections 20 is adjusted to be lower than that of the liquid-absorbent core 4 so that most of menstrual discharge may move to the liquid-absorbent core 4 only after it has moved from the low density sections 21 to the high density sections 20. In this way, blots of menstrual discharge on the liquid-absorbent core 4 as well as on the diffusing sheet 5 is well concealed from the user's eye, since, in the diffusing sheet 5, most of menstrual discharge is collected in the high density sections 20 underlying the stripe-zones 8 and at the same time rapidly diffuses longitudinally of these sections 20 toward longitudinally opposite ends of the napkin 1. Thus, menstrual discharge is absorbed by the core 4 also at these ends of the napkin 1.

In the napkin 1 according to the invention, the spun bond nonwoven fabric used for the diffusing sheet 5 in the embodiment shown and described above may be replaced by a nonwoven fabric of the other types such as a melt bond nonwoven fabric, or a fibrous web in which fibers are merely accumulated. The stripe-zones 8 made of a hydrophobic synthetic resin may be formed by extruding strips or filaments of a thermoplastic synthetic resin each having a width "W"=0.05 to 1.5 mm and a thickness=0.01 to 0.08 mm onto the surface(s) of the continuously fed diffusing sheet 5 and bonding them to the surface(s) under a pressure. Alternatively, filaments of hot melt adhesive may be applied to the surface(s) of the sheet 5 or the surface(s) of the sheet 5 may be partially heated to form film-like stripes. It is possible to reinforce these stripe-zones 8 by partially connecting each pair of adjacent stripe-zones 8 in a ladder-like fashion so far as such reinforcement does not affect diffusion of menstrual discharge in the longitudinal direction. It should be understood that the connections for reinforcement are preferably spaced one from another longitudinally of the stripe-zones 8 by a distance of 20 mm or longer. The stripe-zones 8 may be appropriately colored to improve a cover-up effect for menstrual discharge. In addition, many, preferably more than half of individual fibers forming the diffusing sheet 5 may be oriented longitudinally or transversely of the napkin 1 to ensure that menstrual discharge can rapidly move to the longitudinally or transversely opposite ends of the liquid-absorbent core 4.

The absorbent article of the invention allows blots of menstrual discharge on the liquid-absorbent core to be effectively concealed from the user's eye without deteriorating the body fluid absorption capacity of the article because of the unique arrangement that the diffusing sheet made of hydrophilic fibers is disposed between the topsheet and the liquid-absorbent core, and because the diffusing sheet is provided on its upper surface with the stripe-zones made of a hydrohobic synthetic resin.

What is claimed is:

1. A disposable absorbent article having a longitudinal axis, transverse axis, a top end and bottom end comprising:

a topsheet consisting a top surface and a lower surface wherein a plurality of spaced apart liquid guide passageways extend vertically from said top surface to said lower surface of said topsheet, said liquid guide passageways comprising openings at an upper end and lower end of said liquid guide passageways, a liquid-absorbent core comprising an upper surface and a lower surface wherein said at least an upper surface is covered with said topsheet, a body fluid diffusing sheet of hydrophilic fibers disposed between said lower surface of said topsheet and said upper surface of said absorbent core;

said body fluid diffusing sheet comprising an upper surface and a lower surface wherein a plurality of spaced apart parallel stripe-zones of hydrophobic synthetic resin extend longitudinally from said top end to said bottom end of said absorbent article wherein said parallel strips are in contact with said lower end of said liquid guide passageways such that the stripe-zones extend across said opening at a lower end of the liquid guide passageways;

and said body fluid diffusing sheet having a fiber density higher in sections underlying said stripe-zones than in sections of the said diffusing sheet extending between each of said stripe-zones.

2. A disposable absorbent article according to claim 1, wherein said stripe-zones are formed from an extrusion-molded thermoplastic synthetic resin.

3. A disposable absorbent article according to claim 1, wherein each of said stripe-zones comprises extrusion-molded films or filaments of a thermoplastic synthetic resin having a width of in a range of approximately 0.05 mm to approximately 1.5 mm.

4. A disposable absorbent article according to claim 1, wherein said stripe-zones are also formed on said lower surface of said body fluid diffusing sheet.

* * * * *